(12) United States Patent
Ivie et al.

(10) Patent No.: US 7,585,524 B2
(45) Date of Patent: Sep. 8, 2009

(54) DIETARY SUPPLEMENT COMPOSITIONS

(75) Inventors: Jeremy Ivie, Ammon, ID (US); Jennifer Kelsey, Ririe, ID (US); Alexander B. Rabovsky, Idaho Falls, ID (US)

(73) Assignee: Melaleuca, Inc., Idaho Falls, ID (US)

( * ) Notice: Subject to any disclaimer, the term of this patent is extended or adjusted under 35 U.S.C. 154(b) by 80 days.

(21) Appl. No.: 11/969,113

(22) Filed: Jan. 3, 2008

(65) Prior Publication Data

US 2009/0175961 A1    Jul. 9, 2009

(51) Int. Cl.
*A01N 65/00*    (2006.01)

(52) U.S. Cl. ..................................... 424/725
(58) Field of Classification Search .............. None
See application file for complete search history.

(56) References Cited

U.S. PATENT DOCUMENTS

2008/0095719 A1*   4/2008   Herrmann et al. ............. 424/48

* cited by examiner

*Primary Examiner*—Michael V Meller
(74) *Attorney, Agent, or Firm*—Fish & Richardson P.C.

(57) ABSTRACT

Dietary supplements are disclosed herein. For example, dietary supplements containing a combination of tripeptides, potassium, pomegranate, and passionflower are provided.

2 Claims, No Drawings

DIETARY SUPPLEMENT COMPOSITIONS

TECHNICAL FIELD

This disclosure relates to dietary supplements. For example, this disclosure provides dietary supplements containing tripeptides and optionally other ingredients such as potassium, pomegranate, and passionflower.

BACKGROUND

Dietary supplements can provide compounds and nutrients in addition to those found in a person's normal diet. In some cases, dietary supplements include more common nutrients that may already be present in a person's diet. For example, vitamin C is a common nutrient that some people believe, if taken in increased amounts, will aid in fighting the common cold or flu. Similarly, some compounds that exhibit antioxidant properties are consumed with the belief that they can provide increased lifespan and/or provide protection against certain diseases, such as cancer. Dietary supplements can be useful to ensure a person receives a full complement of the vitamins, minerals, and other nutrients recommended by doctors and nutritionists.

SUMMARY

In general, this disclosure provides dietary supplements. For example, this disclosure provides dietary supplements containing one or more tripeptides. In some cases, a dietary supplement provided herein can include a tripeptide, potassium, pomegranate or pomegranate extract, and/or passionflower or a passionflower extract. The dietary supplements provided herein can be used to maintain healthy blood pressure and optimum health.

In general, one aspect of this document features a dietary supplement comprising a tripeptide, potassium, pomegranate, and passionflower. The tripeptide can be present from about 35 percent to about 45 percent by weight. The potassium source can be present from about 10 percent to about 25 percent by weight. The pomegranate can be present from about 2 percent to about 5 percent by weight. The passionflower can be present from about 2 percent to about 5 percent by weight. The dietary supplement can be a pill, a powder, or a liquid.

In another aspect, this document features a dietary supplement comprising a milk protein hydrolysate, potassium, and plant-derived flavonoids, alkaloids, and glycosides. The milk protein hydrolysate can comprise a Val-Pro-Pro tripeptide. The milk protein hydrolysate can comprise an Ile-Pro-Pro tripeptide. The supplement can comprise pomegranate comprising the flavonoids. The supplement can comprise passionflower comprising the alkaloids and glycosides.

In another aspect, this document features a dietary supplement consisting of between 250 and 325 mg of tripeptide, between 70 and 180 mg of a potassium source, between 14 and 36 mg of passionflower, and between 14 and 36 mg of pomegranate. The dietary supplement can consist of about 280 to about 290 mg of hydrolyzed casein, about 22 to about 28 mg of the pomegranate, about 22 to about 28 mg of the passionflower, and about 90 to 105 mg of the potassium source.

Unless otherwise defined, all technical and scientific terms used herein have the same meaning as commonly understood by one of ordinary skill in the art to which this disclosure pertains. Although methods and materials similar or equivalent to those described herein can be used in the practice or testing, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments are set forth in the accompanying drawings and the description below. Other features, objects, and advantages will be apparent from the drawings and detailed description, and from the claims.

DETAILED DESCRIPTION

In general, this disclosure provides dietary supplements. For example, this disclosure provides dietary supplements containing one or more tripeptides. In some cases, a dietary supplement provided herein can include a tripeptide, potassium, pomegranate or pomegranate extract, and/or passionflower or a passionflower extract.

A tripeptide included in a dietary supplement provided herein can be a hydrolyzed tripeptide. In one embodiment, a dietary supplement provided herein can contain tripeptides found in a milk protein hyrdolysate such as Val-Pro-Pro and Ile-Pro-Pro.

Any appropriate method can be used to obtain tripeptides. For example, enzymatic hydrolysis of casein can be used to obtain a preparation of tripeptides. A dietary supplement provided herein can contain any amount of a tripeptide. For example, a dietary supplement can contain from about 0.01 µg to about 1 g (e.g., from about 0.01 µg to about 750 mg; from about 0.01 µg to about 500 mg; from about 0.1 µg to about 1 g; from about 1 µg to about 1 g; from about 10 µg to about 1 g; from about 100 µg to about 1 g; from about 10 µg to about 750 mg; or from about 0.1 mg to about 750 mg) of tripeptides. In some cases, between about 25 percent to about 50 percent (e.g., between about 25 to about 45 percent; between about 25 to about 40 percent; between about 35 to about 50 percent; or between about 35 to about 45 percent) of a dietary supplement can be tripeptides.

In some cases, a dietary supplement provided herein can include optional ingredients such as extracts of any type of fruit or plant. For example, a dietary supplement can include an extract of a pomegranate (e.g., *Punica granatum*). Extracts of pomegranate, including pomegranate juice can have natural antioxidant characteristics. Any type of pomegranate or pomegranate extract can be included in a dietary supplement provided herein. Pomegranate extracts can be in any form, for example, a solution, a powder, or a soluble powder.

A dietary supplement provided herein can contain any number of different pomegranate extracts. For example, a dietary supplement can contain one, two, three, four, five, six, seven, eight, nine, ten, or more different pomegranate extracts. Any appropriate method can be used to obtain pomegranate extracts. For example, ethanol/water can be used to obtain a preparation of pomegranate extracts. In some cases, pomegranate extracts can be extracted from naturally-occurring sources. In some cases, a water extraction process can be performed using pomegranate as a source material to obtain a preparation of pomegranate extract. A dietary supplement provided herein can contain any amount of a pomegranate extract. For example, a dietary supplement can contain from about 0.01 µg to about 1 g (e.g., from about 0.01 µg to about 750 mg; from about 0.01 µg to about 500 mg; from about 0.1 µg to about 1 g; from about 1 µg to about 1 g; from about 10 µg to about 1 g; from about 100 µg to about 1 g; from about 10 µg to about 750 mg; or from about 0.1 mg to about 750 mg) of pomegranate extract. In some cases, between about 2 percent to about 5 percent (e.g., between about 2 to about 4 percent; between about 2 to about 3 percent; between about 3 to about 5 percent; or between about 4 to about 5 percent) of a dietary supplement can be a pomegranate extract.

In some cases, a dietary supplement provided herein can include optional ingredients such as an extract from a plant in the genus *Passiflora* (e.g., a passionflower extract). Any type of *Passiflora* plant extract (e.g., passionflower extract) can be included in a dietary supplement provided herein. Examples of *Passiflora* plant extracts include, without limitation, standardized or non-standardized passionflower extracts. *Passiflora* plant extracts (e.g., passionflower extracts) can be in any form, for example, a solution, a powder, or a soluble powder.

A dietary supplement provided herein can contain any number of different *Passiflora* plant extracts. For example, a dietary supplement can contain one, two, three, four, five, six, seven, eight, nine, ten, or more different *Passiflora* plant extracts. Any appropriate method can be used to obtain *Passiflora* plant extracts. For example, ethanol/water extraction or water extraction can be used to obtain a preparation of passionflower extracts. A dietary supplement provided herein can contain any amount of a *Passiflora* plant extract. For example, a dietary supplement can contain from about 0.01 µg to about 1 g (e.g., from about 0.01 µg to about 750 mg; from about 0.01 µg to about 500 mg; from about 0.1 µg to about 1 g; from about 1 µg to about 1 g; from about 10 µg to about 1 g; from about 100 µg to about 1 g; from about 10 µg to about 750 mg; or from about 0.1 mg to about 750 mg) of *Passiflora* plant extract. In some cases, between about 2 percent to about 5 percent (e.g., between about 2 to about 4 percent; between about 2 to about 3 percent; between about 3 to about 5 percent; or between about 4 to about 5 percent) of a dietary supplement can be a *Passiflora* plant extract.

In general, extraction is a process whereby the desired constituents of a source material (e.g., a fruit, plant, or plant part) are removed using, for example, a solvent. To produce an extract, fruit, plant, or plant part material can be first cleaned and dried, if necessary. Drying can be performed naturally (e.g., by air drying) or artificially (e.g., using warm-air fans or conveyor dryers). Fruit, plant, or plant part material can then be ground, cut, or shredded using, for example, hammer action, pressure, friction, or impact cutting. Methods of removing the desired constituents from the plant material include, without limitation, organic solvent extraction, supercritical gas extraction, and steam distillation.

The ability to use a number of different solutes, diluents, extractants, and aqueous phases as well as rapid extraction kinetics for many separations, can make solvent extraction a powerful separation method. By way of example, there are a number of procedures for organic solvent extraction, including maceration (soaking and agitating the fruit, plant, or plant part material with a solvent), percolation (repeated rinsing of the fruit, plant, or plant part material with a solvent), and countercurrent extraction (continuous flow of a solvent in the opposite direction as the fruit, plant, or plant part material).

Representative solvents include, without limitation, ethanol, or ethanol/water. Aqueous extracts, such as decoctions (produced by boiling the fruit, plant, or plant part material such as hard tissues), infusions (produced by steeping the fruit, plant, or plant part material such as soft tissues), or macerations, can also be produced. In some cases, numerous separation procedures can be used to further purify desired components or remove unwanted or contaminating components. Examples of such separation procedures include, without limitation, decanting, filtration, sedimentation, centrifugation, heating, adsorption, precipitation, chromatography, or ion exchange. The resulting products can be subsequently evaporated, vaporized, lyophilized, spray dried, freeze-dried, or vacuum dried.

In some cases, a dietary supplement provided herein can include optional ingredients such as potassium. For example, a dietary supplement provided herein can contain a potassium salt such as potassium chloride. A dietary supplement provided herein can contain any number of different sources of potassium. For example, a dietary supplement can contain one, two, or more different sources of potassium. Any appropriate method can be used to obtain a source of potassium (e.g., potassium chloride). A dietary supplement provided herein can contain any amount of a source of potassium. For example, a dietary supplement can contain from about 0.01 µg to about 1 g (e.g., from about 0.01 µg to about 750 mg; from about 0.01 µg to about 500 mg; from about 0.1 µg to about 1 g; from about 1 µg to about 1 g; from about 10 µg to about 1 g; from about 100 µg to about 1 g; from about 10 µg to about 750 mg; or from about 0.1 mg to about 750 mg) of potassium chloride. In some cases, between about 10 percent to about 25 percent (e.g., between about 10 to about 20 percent; between about 10 to about 15 percent; between about 15 to about 25 percent; or between about 20 to about 25 percent) of a dietary supplement can be a potassium source.

In some cases, a dietary supplement provided herein can contain a tripeptide, potassium (including potassium sources, such as potassium chloride), an extract of pomegranate, and an extract of passionflower. The weight ratio of tripeptide to other, optional ingredients (e.g., potassium, extract of pomegranate, extract of passionflower, other additives) can be from about 35:65 to about 45:55. The ratio can be based, for example, on the dry weight of each ingredient or extract.

In some cases, a dietary supplement provided herein can be designed to contain the following: Casein Hydrolysate (570 mg), pomegranate powder (50 mg), passionflower extract (50 mg), and potassium chloride (197.8 mg).

A dietary supplement provided herein can be ingested. For example, a dietary supplement can be administered orally or intragastrically. In some cases, a dietary supplement provided herein can be administered by other routes such as nasally, intravenously, intramuscularly, subcutaneously, sublingually, intrathecally, or intradermally. Any amount of a dietary supplement provided herein can be administered to a mammal. The dosages of a dietary supplement can depend on many factors, including the mode of administration. The amount of tripeptide, potassium, extract of pomegranate, and extract of passionflower contained within a single dose of a dietary supplement can be an amount that can effectively maintain a desired result in a mammal without inducing significant toxicity. For example, a dietary supplement can be formulated in a dose such that an individual receives from about 500 mg up to about 650 mg of tripeptide, from about 140 mg up to about 360 mg of potassium chloride, from about 28 mg up to about 72 mg of pomegranate extract, from about 28 mg up to about 72 mg of passionflower extract, per serving. Typically, a dietary supplement can be administered in an amount from about 1400 mg up to about 1600 mg per serving.

A dietary supplement provided herein can be in the form of a liquid, solution, suspension, pill, capsule, tablet, gelcap, powder, or gel. For oral administration, tablets or capsules can be prepared by conventional means with acceptable excipients such as binding agents, fillers, lubricants, disintegrants, or wetting agents. The tablets can be coated, if desired. Liquid preparations for oral administration can take the form of, for example, solutions, syrups, or suspension, or they can be presented as a dry product for constitution with saline or other suitable liquid vehicle before use. Dietary supplements of the type described herein also can contain acceptable additives such as suspending agents, emulsifying agents, non-aqueous vehicles, preservatives, buffer salts, flavoring, coloring, and sweetening agents as appropriate. Preparations for oral administration also can be suitably formulated to give controlled release of the ingredients.

In some cases, a dietary supplement provided herein can contain an acceptable carrier for administration to a mammal (e.g., a human), including, without limitation, sterile aqueous, or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Acceptable carriers also can include physiologically acceptable aqueous vehicles (e.g., physiological saline) or other known carriers appropriate to specific routes of administration.

As described herein, a dietary supplement can be used to maintain favorable blood pressure in a mammal. Blood pressure can be examined using any appropriate method. For example, a sphygmomanometer (also known as a "blood pressure cuff") can be applied to the arm of a human between the elbow and the shoulder. The cuff can be filled with air, thereby applying pressure to the brachial artery, until such time that the brachial artery is occluded. A small amount of pressure is released from the cuff until the Korotkoff sounds are auscultated near the brachial artery at the human's elbow, usually with the aid of a stethoscope. The pressure at which the Korotkoff sounds first appear is referred to as the systolic blood pressure and indicates blood pressure as the blood is pumped from the human's aorta. Pressure is continually released from the sphygmomanometer until such time that the Korotkoff sounds are no longer auscultated. This pressure is the diastolic pressure, or the "resting" pressure when blood is returning to the heart. Blood pressure is usually reported as a ratio of systolic pressure to diastolic pressure, e.g., 120/80. In many cases, pressure is measured in mm Hg.

Blood pressure can be continually or intermittently monitored over a period of time, e.g., once a day, once a week, once a month. A blood pressure trend may indicate the effectiveness of a dietary supplement to lower or maintain healthy blood pressure.

The following examples further describe dietary supplements but do not limit the scope of the inventive concepts described in the claims.

EXAMPLES

Example 1

Dietary Supplement Formulation

Casein hyrdolysate, including Val-Pro-Pro and Ile-Pro-Pro was added to a selection of binding agents, an extract of pomegranate, an extract of passionflower, and an amount of potassium chloride to create a mixture. The mixture was blended and compressed into tablet form to provide a dietary supplement containing 40% by weight tripeptide, 3.5% by weight extract of pomegranate, 3.5% by weight extract of passionflower, and 13.7% by weight potassium chloride.

Other Embodiments

It is to be understood that while the above embodiments have been described in conjunction with the detailed description thereof, the foregoing description is intended to illustrate, and not limit the scope of the inventive concepts, which are defined by the scope of the appended claims. Other aspects, advantages, and modifications are within the scope of the following claims.

What is claimed is:

1. A dietary supplement consisting of between 250 and 325 mg of tripeptide, between 70 and 180 mg of a potassium source, between 14 and 36 mg of passionflower, and between 14 and 36 mg of pomegranate.

2. The dietary supplement of claim 1, wherein said dietary supplement consists of about 280 to about 290 mg of hydrolyzed casein, about 22 to about 28 mg of said pomegranate, about 22 to about 28 mg of said passionflower, and about 90 to 105 mg of said potassium source.

* * * * *